United States Patent [19]

Schwarz

[11] 4,287,888
[45] Sep. 8, 1981

[54] IRRIGATING APPLIANCE FOR FEMALE HYGIENE

[76] Inventor: Günter Schwarz, Steinacherstr. 67, 8804 Au, Switzerland

[21] Appl. No.: 86,581

[22] PCT Filed: Mar. 13, 1979

[86] PCT No.: PCT No. PCT/CH79/00039

§ 371 Date: Nov. 13, 1979

§ 102(e) Date: Oct. 19, 1979

[87] PCT Pub. No.: WO79/00750

PCT Pub. Date: Oct. 4, 1979

[30] Foreign Application Priority Data

Mar. 13, 1978 [CH] Switzerland .................. 2682/78

[51] Int. Cl.³ ............................................. A61M 3/00
[52] U.S. Cl. ..................................... 128/239; 128/251
[58] Field of Search ............... 128/239, 241, 243, 245, 128/229, 251, 242

[56] References Cited

U.S. PATENT DOCUMENTS

| 1,338,464 | 4/1920 | Shafer | 128/239 |
| 1,531,213 | 3/1925 | Nimmer | 128/239 |
| 2,683,456 | 7/1954 | Pierson | 128/239 X |
| 3,916,896 | 11/1975 | Ballard | 128/239 |

Primary Examiner—John D. Yasko
Attorney, Agent, or Firm—Toren, McGeady and Stanger

[57] ABSTRACT

The irrigating appliance has a shaft-like hollow member(90), whose one end can be connected to the bathroom shower or douche tube. At the front end there are a plurality of outlets (138) for forming a miniature douche for irrigating the inside of the vagina. A larger opening (132) at the rear end of the hollow member leads to the flowing away of most of the water supplied to the appliance and prevents a too high water pressure at the front outlets (138). From the rear end of hollow member (90) a plate-like member (96) extends radially outwards to one side, so that the water discharged from the larger opening (132) flows along said member (96). This plate-like member (96) limits the distance by which the shaft-like hollow member (90) can be inserted into the vagina.

15 Claims, 14 Drawing Figures

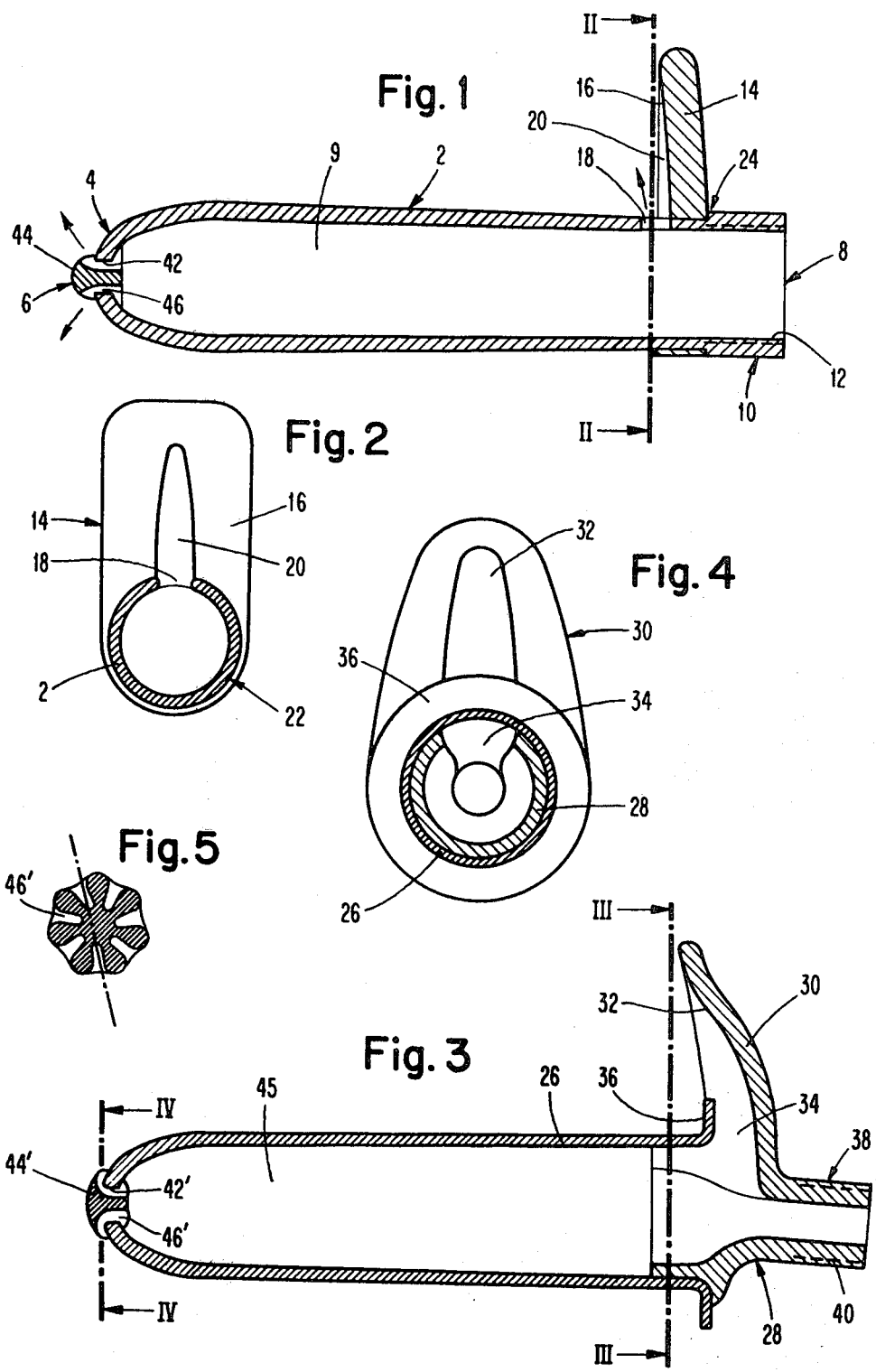

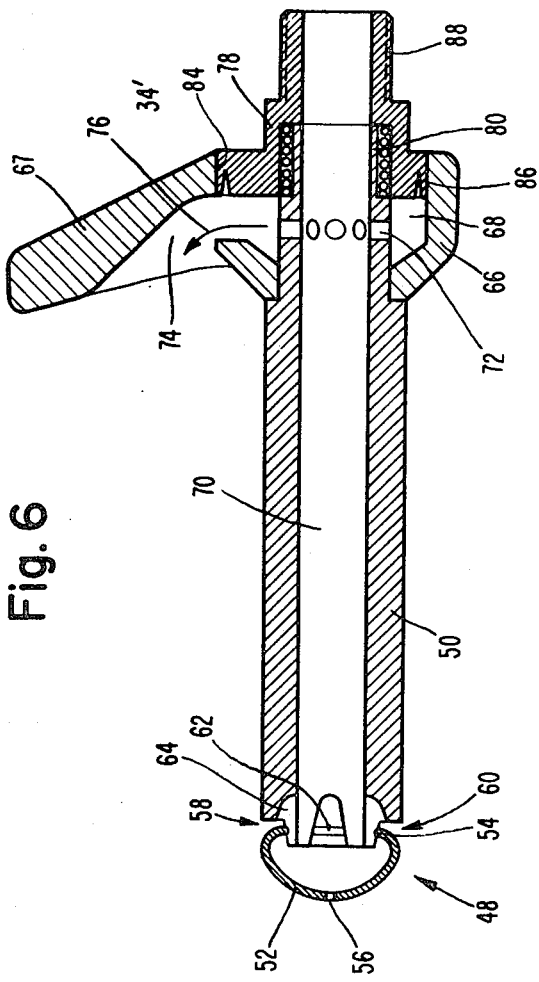

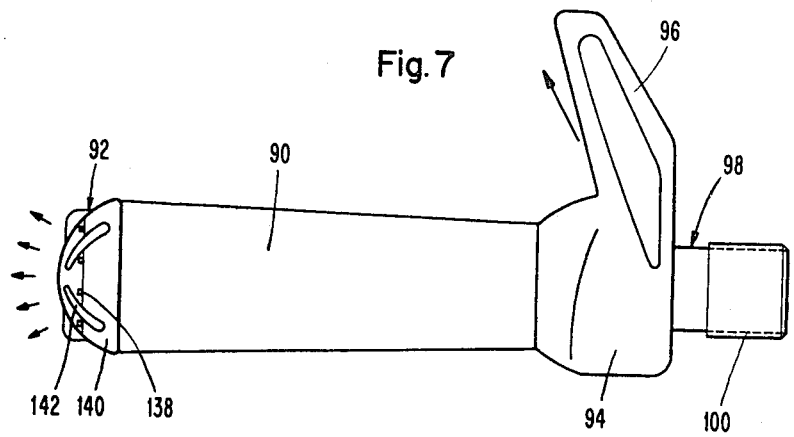
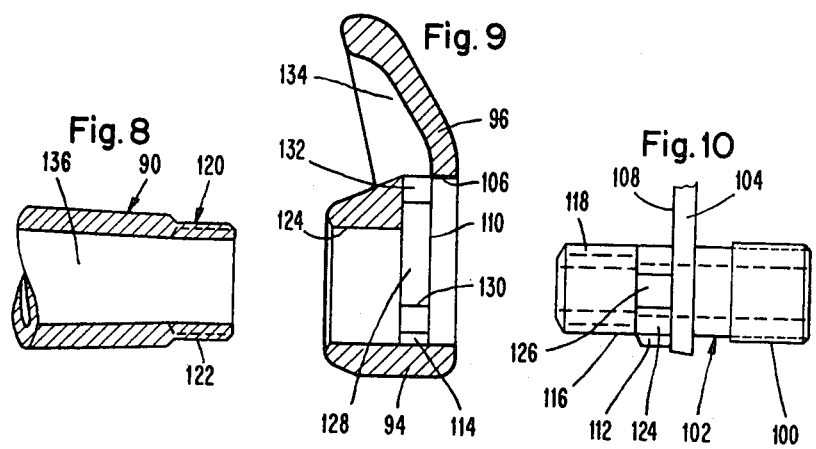
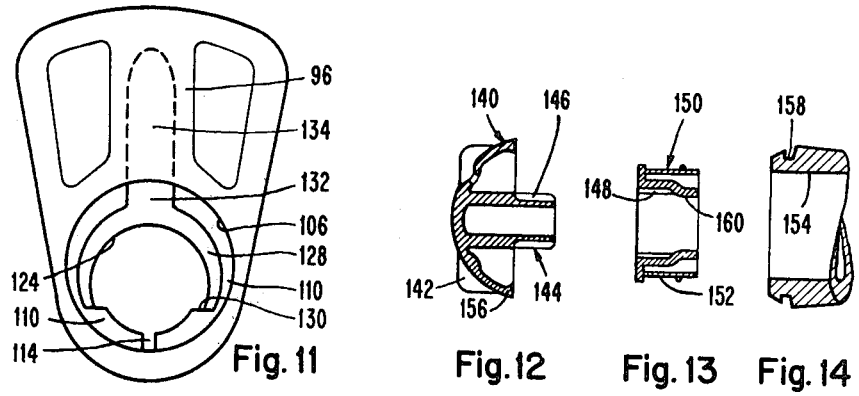

IRRIGATING APPLIANCE FOR FEMALE HYGIENE

The invention relates to an irrigating appliance for female hygiene with a shaft-like member having a cavity with an inlet and at least one outlet for an irrigating liquid. In a known irrigating appliance of this type on a shaft-like hollow member a device is provided such as, e.g. a rubber bulb, so that through manually operating the device a limited quantity of a washing or irrigating liquid is made available for irrigating the vagina. Although such a known irrigating appliance has the advantage that a prepared irrigating liquid can be used without special additional devices, the overall operation, including the subsequent cleaning of the appliance, particularly when a thorough irrigation is desired, is linked with complicated and generally unpleasant manipulations which discourage regular use.

U.S. Pat. No. 3,916,896 describes a hygienic irrigating appliance which can be connected to a pressure tube and which at the front end of a tubular member has numerous water outlets. Further closable outlets are provided on the periphery of the rear end of the member in the vicinity of a funnel-shaped extension defining in insertion into the anus or vagina. Said front and rear outlets bring about a fan or spray-like discharge of the water. When the appliance is connected to the water mains, particularly when the rear outlet is closed the water is discharged at a considerable pressure and/or high speed, so that the water jets can injure the inside of the human body. There is also a correspondingly high counterpressure in the appliance which prevents the connection thereof to a conventional pressure tube due to the risk of destroying the tube. Finally this known appliance is of complicated construction and difficult to clean due to the numerous co-operating parts movable with respect to one another.

The problem of the present invention is to provide an irrigating appliance for female hygiene which does not have the disadvantages referred to hereinbefore and which ensures agreeable use by the woman with a low water discharge speed from the front outlets, so that there is little to prevent its widespread and frequent use. This problem is solved by an irrigating appliance with the features of claim 1. The subclaims contain advantageous developments of this irrigating appliance. Experience has shown that even after prolonged regular use of the irrigating appliance no disadvantageous effects occur and the intended hygienic action is fully ensured.

It has been found that conventional domestic mixed water systems provide water with an adequate relative sterility, which is ideally suited for irrigating or washing the vagina, i.e. for flushing away undesired bacteria, contaminants, etc.

According to an advantageous embodiment of the invention at least one outlet is provided on the side of the engagement member directed towards the end of the penis-shaped member. As a result part of the irrigating liquid flowing into the cavity is lead off through this outlet to the outer body surfaces of the woman located in the vicinity of the vaginal opening, such as in particular the clitoris. By partly or completely closing this outlet, e.g. with the finger of one hand the pressure of the irrigating liquid discharged from the other outlets, e.g. at the front end of the member can be controlled. In the vicinity of this outlet a convexity can be provided in the engagement member which issues approximately tangentially into the outlet. As a result the flow discharged from the said outlet is concentrated on a particular area of the woman's body, e.g. the clitoris so that a particularly intense and pleasant feeling is obtained.

The discharge device at the rounded front end of the shaft-like hollow member can advantageously have a distributing device which can be inserted in mushroom-shaped manner into an axial opening of the hollow member with the handle and is fixed, so that the irrigating liquid is deflected by the distributing device in a fan or ray-shaped manner in substantially radial direction. On axial displacement of the hollow member in the vagina the entire surface of the vagina is directly flushed by the irrigating liquid discharged through the outlet.

The invention is described in greater detail hereinafter relative to non-limitative embodiments and the attached drawings, wherein show:

FIG. 1 an axial section through a first embodiment of the irrigating appliance.

FIG. 2 a cross-section along the line II—II of FIG. 1.

FIG. 3 an axial section through the second embodiment of the irrigating appliance.

FIG. 4 a cross-section along the line III—III of FIG. 3.

FIG. 5 a cross-section through the distributing device of the discharge device along line IV—IV of FIG. 3.

FIG. 6 an axial section through a third embodiment of the irrigating appliance.

FIG. 7 a side view of a forth embodiment of the irrigating appliance.

FIG. 8 a cross-section through the rear end of the shaft-like member of the irrigating appliance of FIG. 7.

FIG. 9 a cross-section through the plate-like engagement member with the shaped-on ring member.

FIG. 10 a cross-section through a coupling member for the tube connection.

FIG. 11 a front view of the engagement member of FIG. 9.

FIG. 12 a douche insert for the front part of the shaft-like member.

FIG. 13 a shaft insert co-operating with the douche insert.

FIG. 14 a cross-section through the front end of the shaft-like member.

The irrigating appliance according to FIG. 1 has an approximately cylindrically shaped member 2 with a rounded front end 4 on which is provided a discharge device 6 for an irrigating liquid flowing through inlet 8. Member 2 surrounds over its entire length a cavity 9. The rear end 10 of the shaft-like member 2 is provided with means, e.g. an internal thread 12 by which the irrigating appliance can be connected to the thread end of a not shown tube of a conventional douche. The means for producing a connection to the tube can be constructed in various known ways. For adaptation to the various known constructions of the tube end of a douche said means, i.e. in the example of FIG. 1 thread 12 can be provided with a suitable adaptor.

A plate-like engagement member 14 is arranged in the area of the rear end of member 2 and on the side directed towards the front end of member 2 has a surface 16 which projects approximately radially from member 2. This surface 16 is intended to engage on the woman's body areas adjacent to the vaginal opening, e.g. the pubic area or the anal area.

In the represented embodiment an outlet 18 is provided immediately in front of surface 16 in member 2, so that the irrigating action in the vicinity of surface 16 is increased. Outlet 18 can issue in an approximately tangential direction to an enlongated convexity 20 provided in surface 16 and directed radially with respect to the hollow member. For connecting the plate-like engagement member 14 to member 2, member 14 contains an opening 22 through which is inserted the hollow member 2.

A shoulder 24 on the rear end 10 of member 2 is used for the positioning of the plate-like engagement member 14. Member 2 and the plate-like member 14 can be made from an elastic plastics material, so that the plate-like member 14 with its opening 22 embraces with pretension the member 2 and is thus reliably secured. It is obvious that the plate-like engagement member 14 can also be constructed in such a way that it projects in two opposite directions from member 2 and not only in one direction as shown in the present embodiment.

The second embodiment of an irrigating appliance according to the invention shown in FIGS. 3 and 4 is fundamentally constructed in the same way as that of FIGS. 1 and 2 with a difference that the shaft-like member 26 passes at its rear end into a connecting member 28 on to whose one side is shaped in radial outwards direction an extension 30, whose side directed towards the front end of member 26 also forms a surface 32 which projects approximately radially outwards from member 26 and which fulfills the same function as surface 16 of the embodiments of FIGS. 1 and 2. The radially directed outlet 34 provided in the also hollow member 26 is located at the end of a flange 36 shaped onto the hollow member 26 and forms the termination of an approximately cylindrical part of the member 26. Connecting member 28 can be connected to the cylindrical part of member 26 by press-fitting, adhesion, screw connection or in other known manners. Connecting member 28 passes in one piece into a connecting piece 38 which has an external thread 40 for fixing the tube end of a douche.

The discharge device at the front, rounded end of hollow member 2 comprises a member 44, 44′ inserted in an axially directed opening 42, 42′ and which has on its periphery a plurality of radially and axially directed recesses 46, 46′ for the outward passage of the irrigating liquid from the inner area 45 of the hollow member, as is shown on a larger scale in FIG. 5. Thus, it constitutes a miniature spray or sprinkler of the type known for showers and douches. However, as shown by the sectional representations of FIGS. 1 and 3 the passage direction through recesses 46, 46′ changes from an axial direction to a radial direction and the passage cross-section also widens outwards (FIG. 5), so that the irrigating liquid is discharged from the end of hollow member 2, 26 with a substantially radial directional component.

The embodiment of FIG. 6 has a discharge device 48 at the front end of a shaft-like member 50, constructed as a hollow cylinder, having a cap 52, whose inwardly directed edge 54 engages in an annular slot of member 50. A central outlet 56 is provided in cap 52, which for this purpose is made from an elastic material. Further outlets 58, 60 and 62 are formed by recesses 64 at the free end of member 50 and a number of these are arranged over its periphery. They widen in the peripheral direction of member 50, so that the liquid is discharged in fan-like manner. Together with cap edge 54 they define outlets 58, 60, 62.

At the rear end of the irrigating appliance of FIG. 6 is provided a ring member 66 which is forced over the recess end of cylindrical hollow member 50, from whose one side engagement member 67 extends outwards in one piece and in shell-shaped manner. The ring member 66 surrounds an annular duct 68, which is inwardly bounded the the outer wall of member 50. The inner area 70 of hollow member 50 is connected via several holes 72 with the annular duct 68, the latter being radially open towards the outside by means of a recess 34′ on the side of convexity 74, so that a powerful liquid flow in the direction of arrow 76 is ensured.

The position of ring member 66 with the engagement member 67 shaped thereon is fixed by an interchangeable connecting member 78, which is firmly mounted on the outer recessed end 80 of member 50 with the interpositioning of sealing material 82 and is sealingly pressed into an opening 84 of ring member 66. The resilient, sealing engagement on the wall of the opening is ensured by a lip 86 which is shaped onto the peripheral edge of the connecting member. As a result of the interchangeability of the connecting member having the connecting thread 88 the irrigating appliance can be connected without difficulty to any douche tube end.

The irrigating appliance of FIG. 7 has a shaft-like member 90 with a slight conical widening towards the front and whose front end there is a closable miniature douche 92. A ring member 94 is connected to the rear end of the shaft-like member 90 and to one side said member 94 passes in one piece into the plate-like engagement member 96. An interchangeable coupling part 98 is inserted in the said ring member, so that by replacing this part it is possible to adapt to various threads 100 and/or different diameters of the terminal socket of a not shown douche tube.

On assembling the irrigating appliance the coupling part 102 shown in FIG. 10 is inserted into the ring member 94 with the plate-like engagement member until its circular disc portion 104 is enclosed in the cylindrical depression 106 of ring member 94 and its radial surface 108 engages on the radial surface 110 of the ring member. Due to the fact that the centre of the circular disc 104 is outwardly displaced relative to the central axis of coupling part 102 and also a projection 112 engages in a slot 114 of ring member 94 the coupling part 102 cannot be turned relative to ring member 94. At its front end the coupling part has a pin 116 with an external thread 118 onto which is screwed the rear cylindrical end 102 of the shaft-like member 90. The cylindrical outer surface 112 of the shaft end engages on the cylindrical surface 124 of an opening of ring member 94. This ensures a firm connection of the plate-like member 96 via ring member 94 with the shaft-like member 90 having the coupling part 102.

The coupling part has a cylindrical portion 124 between disc 104 and the connecting thread 118 for the shaft-like member and in said portion there are two diametrically facing openings 126 through which the water can flow from the inside through the inner bore of the coupling part radially out into an annular duct 128 located in the ring member 94. At the bottom this annular duct terminates at both ends in a shoulder 130 of the ring member, which is at the same height as the lower edge of opening 126 of the coupling part. Towards the front of the appliance the annular duct is bounded by the radial wall 128 and towards the rear by the surface 108 of the circular disc 104. Towards the top and/or towards the side of ring member 94 where the plate-like member 96 is located, annular duct 128 passes via an opening 132 in the wall of ring member 94 into a radially outwardly extending channel 134 formed as a convexity in the front side of the plate-like member 96.

In this way a dense jet of water can flow outwards along the plate-like member 96 and this corresponds to the main quantity of the water flowing through the coupling part 98. When the shaft-like member 90 is inserted in the vagina this jet of water is directed against the clitoris, so that if desired there is an intense stimulating action. However, it is obvious that this channel 134 and/or the plate-like member 96 can be directed downwards instead of upwards towards the clitoris.

A much smaller quantity of water passes via inner area 136 of the shaft-like member 90 to the front end of the irrigating appliance and can escape through a plurality of small holes 138, in much the same way as a sprinkler. By turning the rounded end cap 140 which carries said holes 138 and which is located at the front end of the appliance it is also possible to stop the discharge of water, as desired. In order to facilitate turning a plurality of rounded ribs 142 are located on cap 140. In order to permit the stopping action the cap is provided with a shaft 144 corresponding to FIG. 12, so that it is shaped like a mushroom. Two grooves 146 on the outside of the shaft and directed axially from its outer end preferably face correspondingly shaped grooves 148 in inner wall of a sleeve-like insert 150 when cap 140 is in the turned open position. The cylindrical outer surface 152 of insert 150 engages on inner wall 154 at the front end of shaft-like member 90. By engaging cap edge 156 provided with an inner bead in a peripheral slot 158 cap 140 is fixed in rotatable manner on the end of shaft-like member 90 and thereby locks insert 150 between it and the shaft-like member 90. On turning cap 140 grooves 146 move away from grooves 148 and are then adjacent to the cylindrical inner wall 160 of insert 150, so that a further flow is prevented. Insert 150 is preferably made from a softer plastics material than the remaining parts of the appliance, so that it engages both with the inner wall 154 of the shaft-like member 90 and with the outer wall of the cap shaft 144.

I claim:

1. In an irrigating appliance for female hygiene with a shaft-like member in which there is a cavity with an inlet (8) and at least one outlet for an irrigating liquid, means for fixing the appliance to one end of a tube connectable to a stationary water supply means located in the vicinity of the rear end of the member and an engagement member arranged in the vicinity of the rear end of the shaft-like member and which projects at least approximately radially from the latter, so that irrigating liquid which flows out when the member is inserted in the woman's vagina is guided over the body surface areas adjacent to the vaginal opening and at least one outlet of the cavity is positioned adjacent to the engagement member side directed towards the front end of the shaft-like member, the improvement comprising a main outlet (18, 34, 34') whose water discharge direction runs radially along one surface of the engagement member positioned adjacent to the latter, an annular duct (68) which embraces the shaft-like member and which is connected with the cavity (70) by a plurality of springs (72), the main outlet (34') being located on an outer periphery point of the annular duct, and a coupling part (102) detachably connected to a ring member (94) and the shaft-like member (90) and having at least one radially directed opening (126) issuing into at least partly annular duct (128) having the main outlet (132) at one point on its periphery.

2. Irrigating appliance according to claim 1, characterised in that a radially outwardly directed convexity is provided in the engagement member on the side directed towards the front end of the shaft-like member (2, 26) and into said convexity is directed the outlet direction of the outlet adjacent to the engagement member.

3. Irrigating appliance according to claim 1, characterised in that the annular duct (68) is formed by a ring member (66) which surrounds the shaft-like member (50) and which directly embraces the outer wall of member (50) and on which is shaped in one piece engagement member (67).

4. Irrigating appliance according to claim 1, characterised is that in the axial direction ring member (66) engages on an annular shoulder of member (50) and on a connecting member (78) mounted on the rear end of the shaft-like member (50) and having attachment means (88).

5. Irrigating appliance according to claim 1, characterised in that the coupling part (102) is constructed in hollow cylindrical manner and carries at each of its two ends a screw thread (118, 100) for connecting the shaft-like member (90) and a tube.

6. Irrigating appliance according to claim 5, characterised in that the coupling part (102) has a disc (104) extending at right angles to its longitudinal direction and which can be inserted in a correspondingly shaped recess (106) of ring member (94), so that it bounds one side of the annular duct (128).

7. In an irrigating appliance for female hygiene with a shaft-like member in which there is a cavity with an inlet (8) and at least one outlet for an irrigating liquid, means for fixing the appliance to one end of a tube connectable to a stationary water supply means located in the vicinity of the rear end of the member and an engagement member arranged in the vicinity of the rear end of the shaft-like member and which projects at least approximately radially from the latter, so that irrigating liquid which flows out when the member is inserted in the woman's vagina is guided over the body surface areas adjacent to the vaginal opening and at least one outlet of the cavity is positioned adjacent to the engagement member side directed towards the front end of the shaft-like member, the improvement comprising a main outlet (18, 34, 34') whose water discharge direction runs radially along one surface of the engagement member positioned adjacent to the latter, a closable miniature douche provided at the front end of the shaft-like member (90), the outlets (138) of the miniature douche being located in a cap-like part (140) rotatably secured to the shaft-like member (90) about the axis thereof, the part (140) having a shaft (144) with at least one longitudinally directed outer groove (146) surrounded by the cylindrical inner wall (160) of a sleeve-like insert (150) inserted in the front end of the shaft-like member (90) and which has at least one longitudinal groove (148) in its cylindrical inner wall (160), so that in an angular position of cap-like part (140) in which the longitudinal grooves (146 and 148) of both parts are superimposed a passage channel is formed which can be closed by turning the sleeve-like part (140).

8. An irrigating appliance for female hygiene comprising: a hollow elongated member having a liquid inlet end and a front end opposite said inlet end; liquid outlet means at said front end for discharge therefrom of an irrigating liquid introduced into said hollow member; means for attaching said appliance at said inlet end to a source of irrigating liquid; an engagement member located proximate said inlet end projecting from said hollow elongated member with a generally radially directed orientation on one side only of said elongated member, said engagement member having thereon a liquid deflection surface facing toward said front end of said hollow elongated member; and additional outlet means located immediately adjacent said deflection surface for producing an essentially unitary outlet stream of liquid directed in a generally radial path from said hollow elongated member flowing along said deflection surface to produce essentially a single liquid stream which may be directed over a limited body surface area adjacent a vaginal opening into which said elongated member is inserted.

9. An appliance according to claim 8 wherein a radially outwardly directed channel-like convexity is provided in said engagement member on the side thereof directed toward said first end of said elongated member with said unitary outlet stream being directed into said convexity.

10. An appliance according to claim 8 wherein said additional outlet means comprise an annular duct extending about said hollow elongated member, a plurality of openings defined in flow communication between the hollow interior of said elongated member and said annular duct and a main outlet in flow communication with said annular duct for defining said unitary outlet stream.

11. An appliance according to claim 10 wherein said annular duct is defined within an annular member which extends around said hollow elongated member and which is attached on the outer wall of said elongated member, said annular member being shaped to define said engagement member.

12. An appliance according to claim 11 wherein said elongated member is formed with an annular shoulder on the inlet end thereof, wherein said annular member is arranged to engage on said annular shoulder of said elongated member and wherein there is further provided a connecting member mounted on said inlet end of said elongated member, said connecting member having formed thereon said means for attaching said appliance to a source of irrigating liquid.

13. An appliance according to claim 8 further comprising an annular member attached at said inlet end of said hollow elongated member and arranged to define an annular duct extending about said elongated member and a coupling part detachably connected with said annular member and said elongated member, said coupling part having at least one radially directed opening issuing into said annular duct, said annular member defining a main outlet of said additional outlet means through which said unitary outlet stream emerges, with said radially directed opening having said main outlet at one point on its periphery.

14. An appliance according to claim 13 wherein said coupling part is constructed as a hollow cylindrical member carrying at each of two ends thereof a screw thread for connecting said elongated member and a tube.

15. An appliance according to claim 14 wherein said coupling part is formed with a disc extending perpendicularly to the longitudinal direction of said elongated member adapted to be inserted in a correspondingly shaped recess formed in said annular member in order to define the boundary on one side of said annular duct.

* * * * *